(12) United States Patent
Vangura

(10) Patent No.: US 9,409,813 B2
(45) Date of Patent: Aug. 9, 2016

(54) HAND-HELD TOOL FOR CUTTING LAMINATED GLASS AND FILM-COVERED GLASS AND METHOD FOR USING SAME

(71) Applicant: Albert Vangura, Gibsonia, PA (US)

(72) Inventor: Albert Vangura, Gibsonia, PA (US)

( * ) Notice: Subject to any disclaimer, the term of this patent is extended or adjusted under 35 U.S.C. 154(b) by 458 days.

(21) Appl. No.: 13/657,741

(22) Filed: Oct. 22, 2012

(65) Prior Publication Data

US 2013/0283985 A1 Oct. 31, 2013

Related U.S. Application Data

(60) Provisional application No. 61/549,345, filed on Oct. 20, 2011.

(51) Int. Cl.
| | |
|---|---|
| *B26B 15/00* | (2006.01) |
| *C03B 33/07* | (2006.01) |
| *C03B 33/12* | (2006.01) |
| *B26D 1/30* | (2006.01) |
| *B26D 1/00* | (2006.01) |

(52) U.S. Cl.
CPC ............... *C03B 33/076* (2013.01); *B26B 15/00* (2013.01); *B26D 1/30* (2013.01); *C03B 33/07* (2013.01); *C03B 33/074* (2013.01); *C03B 33/12* (2013.01); *B26D 2001/006* (2013.01); *B26D 2001/0066* (2013.01); *Y10T 83/04* (2015.04)

(58) Field of Classification Search
CPC .... C03B 33/076; C03B 33/074; C03B 33/12; C03B 33/07; B26B 15/00; B26D 2001/006; B26D 2001/0066; Y10T 83/04

USPC ................. 83/13, 879–887; 30/228–230, 371
See application file for complete search history.

(56) References Cited

U.S. PATENT DOCUMENTS

| | | | |
|---|---|---|---|
| 2,934,822 A | 5/1960 | Docken | |
| 3,808,682 A | 5/1974 | Sumida | |
| 4,173,069 A | 11/1979 | Sidenstick et al. | |
| 5,566,454 A | 10/1996 | Eisenbraun | |
| 5,772,823 A * | 6/1998 | Rusch et al. | .......... 156/108 |
| 5,992,024 A | 11/1999 | Rogers | |
| 5,993,303 A | 11/1999 | Fladgard et al. | |
| D443,806 S | 6/2001 | Fladgard et al. | |
| 7,637,016 B2 | 12/2009 | Fladgard et al. | |
| 2003/0029043 A1 | 2/2003 | Fladgard et al. | |
| 2004/0050223 A1 | 3/2004 | Renecker et al. | |
| 2006/0213343 A1 | 9/2006 | Edwards et al. | |

FOREIGN PATENT DOCUMENTS

| | | |
|---|---|---|
| EP | 2177482 | 4/2010 |
| WO | 2006104523 | 5/2006 |

* cited by examiner

*Primary Examiner* — Omar Flores Sanchez
(74) *Attorney, Agent, or Firm* — Blynn L. Shideler; Krisanne Shideler; BLK Law Group

(57) ABSTRACT

An apparatus for cutting laminated glass and film-covered glass includes a powered hand-held tool with a blade set including two static cutting blades and one dynamic, reciprocating cutting blade. The reciprocating cutting blade moves between the two static cutting blades which are rigidly mounted to the tool head. The left and right static cutting blades were spaced apart by about 0.250 inches, and the cutting blade had a thickness of about 0.200-0.250 inches. The clearance between the reciprocating and each static blade is between about 0.005-0.025 inches.

10 Claims, 2 Drawing Sheets

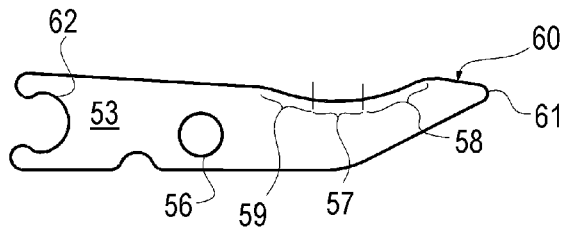
FIG. 4
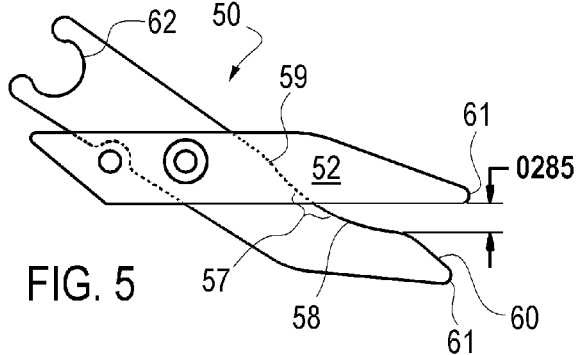
FIG. 5
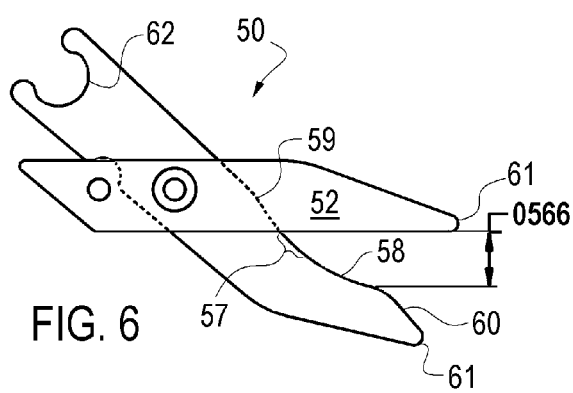
FIG. 6
FIG. 7

HAND-HELD TOOL FOR CUTTING LAMINATED GLASS AND FILM-COVERED GLASS AND METHOD FOR USING SAME

RELATED APPLICATIONS

This application claims priority to U.S. provisional patent application Ser. No. 61/549,345 filed Oct. 20, 2011, entitled "A Hand-Held Tool For Cutting Laminated Glass And Film-Covered Glass And Method For Using Same."

BACKGROUND OF THE INVENTION

1. Field of the Invention

The present invention relates to a relates to a hand held tool for cutting laminated glass and film-covered glass, such as automotive windshields and architectural windows, and an associated method for cutting laminated glass and film-covered glass.

2. Background Information

Laminated glass, which is a type of safety glass, utilizes two or more regular or specially strengthened glass sheets bonded together with a special plastic interlayer to form a clear, see-through barrier with enhanced impact and shatter resistance. Polyvinyl butyral (PVB) plastic is commonly used as the interlayer which enhances the glass further by increasing sound insulation and blocking nearly 99% of ultraviolet radiation. The interlayer maintains the layers of glass bonded even when broken, and the relative high strength of the interlayer prevents the glass from breaking up into large sharp pieces. This produces a characteristic "spider web" cracking pattern when the impact is not enough to completely pierce the laminated glass. Laminated glass is normally used when there is a possibility of human impact or where the glass could fall if shattered. Laminated glass is standard in automobile windshields and is routinely used in building architectural windows or curtain walls (a non-structural outer covering of a building), skylights, and in prisons. More recently, laminated glass is used for blast and hurricane protection for architectural windows.

Automobile windshields are a clear, see-through wind barrier which provides impact resistance from insects, road debris, vandalism, etc . . . , roof crush resistance, airbag support and resistance to occupant ejection. Windshields can become damaged during normal use and during vehicle crashes. When windshields fracture, the glass fragments are contained and occupant injury risk is minimized. It should be noted that the term windshield is used generally throughout North America while the term windscreen is the usual term in the British Isles and Australasia for all vehicles. Rear windows of automobiles are also constructed of glass laminates.

During automobile crashes, there are instances when the vehicle occupants become trapped within the vehicle, possibly in need of emergency assistance, but where the occupants cannot be accessed via the doors. When this occurs, emergency personnel are required to remove the windshield or rear window to access the occupants. There are two methods employed for windshield removal: 1) blunt impact or 2) cutting. Blunt impact with an object like a hammer or a fire axe can fracture or tear the windshield. Handheld or powered saws can cut windshield glass after creating an access hole. Each of these methods increases the risk of injury to the patients/vehicle occupants and/or the emergency personnel by flying glass debris and increased extrication time. The power saws additionally create a large amount of harmful silica dust, discussed further below, as it ribs apart a ribbon of the windshield that is slightly wider than the saw blade.

During normal use, windshields can become damaged by impacts from road debris or other materials and require replacement. After replacement, the vehicle inspection stickers must be replaced or transferred from the old windshield. Technicians routinely transfer the inspection stickers intact with a portion of the windshield by trimming the glass, protecting the sharp edges with tape and placing them on the vehicle dashboard. This process can be time consuming and increases the risk of personal injury.

Plastic films are commonly used to cover laminated and un-laminated glass to provide additional resistance to impact, fire, UV light, sound and blast.

Silica is a mineral compound made up of one silicon atom and two oxygen atoms ($SiO_2$). Crystalline silica is formed when silica molecules are lined up in order and in crystal form. Crystalline silica is a component of glass and has been used in many other industries such as blast furnaces, cement manufacturing, glass and concrete mixing product manufacture, ceramics, clay, china pottery, electronic, foundry, sandblasting and manufacturing abrasives, and many construction activities. Occupations having a high potential for exposure to crystalline silica dust (aka respirable quartz) are metal, coal, and nonmetal (except fuels) mining; foundry, stone clay, and glass production work; and agricultural, chemical production, highway repair, and tuck-pointing work. Thus silica dust is a known inhalation hazard. Workers may be at risk of silicosis from exposure to silica dust when high-velocity impact shatters the sand into smaller, respirable (<0.5 to 5.0 μm in diameter) dust particles. According to the American Thoracic Society silicosis is a disease where scar tissue forms in the lungs and reduces the ability to extract oxygen from the air. Symptoms of silicosis can be acute, accelerated, or chronic. According to the National Institute for Occupational Safety and Health acute silicosis may develop within weeks and up to 5 years after breathing large amounts of crystalline silica. Accelerated silicosis may develop shortly after exposure to high concentrations of respirable crystalline silica, whereas chronic silicosis occurs after 10 years of exposure to relatively low concentrations of crystalline silica. OSHA has estimated that more than 2 million workers are exposed to crystalline silica dust in the general, maritime, and construction industries, and that more than 100,000 workers have high-risk exposure to airborne silica dust through construction and mining operations. Further it has been estimated that there were an estimated 3,600-7,300 newly recognized silicosis cases per year in the United States from 1987 to 1996 and that between 1990 and 1996, 200-300 deaths per year were known to have occurred where silicosis was identified as a contributing cause on death certificates. Further, the International Agency for Research on Cancer classified crystalline silica as a known human carcinogen with exposure to crystalline silica associated with an increased risk of developing lung cancer. Previous studies also documented an association between airborne silica exposure and other health problems, including chronic obstructive pulmonary disease, rheumatoid arthritis, scleroderma, Sjogern's syndrome, lupus, and renal disease.

In fields other than glass, shearing tools have been designed such as disclosed in U.S. Pat. No. 7,637,016, which is incorporated herein by reference, which discloses hand-held cutting tools used to cut fiber-cement siding. U.S. Published Patent Application 2006-0213343, which is also incorporated herein by reference, discloses waste ejecting blade assemblies for hand-held cutting tools and methods for cutting fiber-cement materials. U.S. Published Patent Application 2004-0050223, which is also incorporated herein by reference, discloses blade assemblies for reciprocating wallboard tools and methods for cutting wallboard. See also U.S. Published Patent Application 2003-0029043, Design Pat. D443,806, U.S. Pat. Nos. 5,993,303, 5,992,024, 5,566,454, 4,173,069, 3,808,682, and 2,934,822 which are also incorporated herein by reference. These tools provide certain advantages for their particular designated work products but fail to provide effective or efficient, or even useful, laminated glass cutting tools as the blade sets of these tools tend to crush the glass layers without shearing the laminating layer resulting in a jammed tool when attempted to be implemented with laminated glass.

A refined method for cutting laminated glass and film-covered glass would minimize personal injury associated with vehicle occupant extrications, as well as laminated glass and film-covered glass repair and replacement. Further, the time needed for cutting will be greatly reduced. Further there is a need to perform such glass processing in a manner that minimizes airborne silica, particularly for Emergency workers, whom do not always take the time needed to don mask or other protective equipment when responding to a vehicle crash.

SUMMARY OF THE INVENTION

One aspect of this invention is directed to an apparatus for cutting laminated glass and film-covered glass and an associated method for cutting laminated glass and film-covered glass. A laminated glass and film-covered glass cutting tool in accordance with this invention may have a hand-held motor unit with a housing, a motor inside the housing, and a switch operatively coupled to the motor to selectively activate the motor. A head having a casing may be attached to the housing of the motor unit. The head may also have a reciprocating drive assembly coupled to the motor.

To meet the need for a laminated glass and film-covered glass cutting tool, the present inventor developed a powered hand-held tool with a blade set including two static cutting blades and one reciprocating cutting blade. The reciprocating cutting blade may be powered, as one representative example, by a Pacific International Tool & Shear, Kingston, Wash. (Model No. SS504). The reciprocating cutting blade moves between the two static cutting blades which are rigidly mounted to the tool head. The left and right static cutting blades were spaced apart by 0.250 inches, and the cutting blade had a thickness of 0.200-0.250 inches. The clearance between the reciprocating and each static blade is between 0.005-0.025 inches.

When cutting laminated glass and film-covered glass in accordance with the present invention, the glass is placed between the open tips of the reciprocating and static cutting blades. The reciprocating cutting blade moves from the open to closed position causing shearing along both sides of the blade to form a cut approximately as wide as the gap between the left and right static blades. The hand tool operator would translate the tool as required as the blade reciprocates between the open and closed positions to cut the laminated glass in a progressive fashion.

The hand-held cutting tool also has a blade set with first and second static blades attached to either the casing or the motor housing, and a reciprocating cutting blade between the first and second static blades. The first static blade may have a first guide surface and a first interior surface. Similarly, the second static blade may have a second guide surface and a second interior surface. The first and second guide surfaces are preferably in a common plane, and the first and second interior surfaces are spaced apart from one another by a gap distance. The reciprocating cutting blade has a body with a first width approximately equal to the gap distance and a blade projecting from the body. The blade has a first side surface facing the first interior surface of the first static blade, a second side surface facing the second interior surface of the second static blade, and a top surface. The first side surface of the blade is preferably spaced apart from the first interior surface of the first finger by 0.005-0.025 laminated glass. Similarly, the second side surface of the blade is spaced apart from the second interior surface of the second static blade by 0.005-0.025 inches.

The top surface of the reciprocating cutting blade may range from flat to angled to concave and may vary with serrations. The reciprocating cutting blade profile may range from straight to curved with single to multiple radii.

It is noted that, as used in this specification and the appended claims, the singular forms "a," "an," and "the" include plural referents unless expressly and unequivocally limited to one referent. The features that characterize the present inventions are pointed out with particularity in the claims which are part of this disclosure. These and other features of the invention, its operating advantages and the specific objects obtained by its use will be more fully understood from the following detailed description and the operating examples.

These and other advantages are described in the brief description of the preferred embodiments in which like reference numeral represent like elements throughout.

BRIEF DESCRIPTION OF THE FIGURES

FIG. 4 is a schematic side elevation view of a dynamic blade of a modified blade set for use in the laminated glass cutting tool of FIG. 1;

FIG. 5 is a schematic side elevation view of the blade set of FIG. 4 in a closed position;

FIG. 6 is a schematic side elevation view of the blade set of FIG. 4 in an open position; and FIG. 7 is a schematic flowchart illustrating the method of removing a windshield according to one aspect of the present invention.

DESCRIPTION OF THE PREFERRED EMBODIMENTS

The present invention is an apparatus and associated method for cutting laminated glass and film-covered glass, such as commonly found in automobile windshields and many laminated architectural windows. Many specific details of certain embodiments of the invention are set forth in the following description and in FIGS. 1-6 to provide a thorough understanding of such embodiments. One skilled in the art, however, will understand that the present invention may have additional embodiments, or that the invention may be practiced without several of the details described in the following description.

Figure 1:
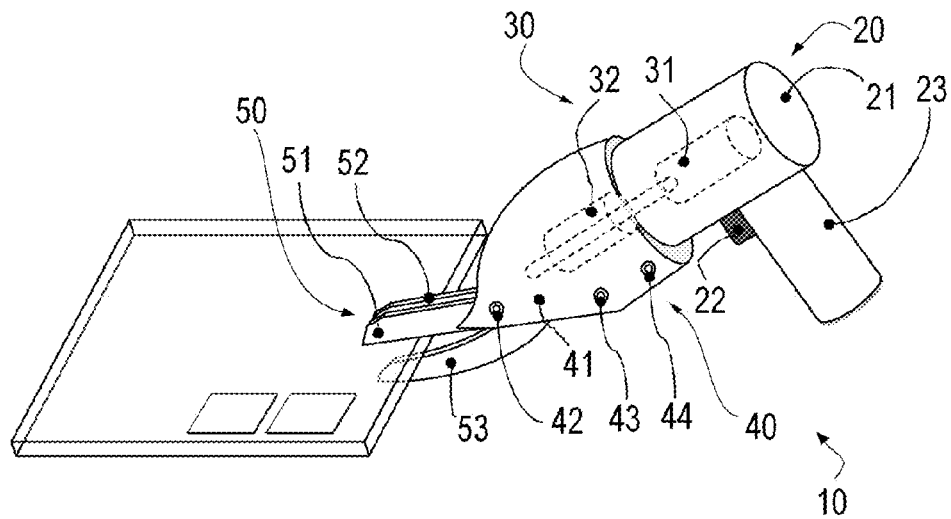
FIG. 1 is schematic isometric view of a laminated glass cutting tool and a blade set engaging a work piece in accordance with one embodiment of the invention.

FIG. 1 is a schematic isometric view of a hand-held cutting tool (10) for cutting a laminated glass or film-covered glass work piece (W). The cutting tool (10) has a housing (20), a drive system (30), a head (40) and a blade set (50).

The housing (20) has a casing (21) which contains the drive system (30), a motor control switch (22) which is operatively coupled with the motor (31) of drive system (30) and a handle (23) for operator gripping. The housing (20) is a hand held unit and preferably operable with a single hand, to allow the user additional freedom, which may be critical in an emergency situation. The housing (20) has the shape of many hand held power tools, which also assists in making the operation of the tool easily and immediately understood by operators, which can be further helpful in emergency situations. Thus there will be no time lost by emergency response personnel, whom would not be expected to utilize the tool (10) daily, re-familiarizing themselves with the operation of the tool (10).

The system or tool (10) can be battery powered as shown, with rechargeable battery pack (not shown), such as a 14.4 V 3.0Ah li-ion battery, received within the handle (23), as generally known in the art. The rechargeable battery pack will typically last for the removal of about 20 automotive windows on a single charge. The tool (10) can also be run from a plug in power source (e.g. conventional 110 v socket) via cord (not shown) also going to handle 23. The battery powered version of the tool (10) as shown is generally preferred for field applications (e.g. automobile windshields in the field), however the cord version of tool (10) can be acceptable for garage applications, or for use in replacing architectural laminated windows. It is also anticipated that the power supply for a given tool (10) could be either a battery pack or plug in cord as selected by the user via appropriate adaptor.

The drive system (30) contains a motor (31) and a transmission (32). The head (40) contains a casing (41) which may be mounted to the housing (20) and/or the drive system (30). The transmission (32) of the drive system (30) converts the rotational power of the motor (31) into reciprocating motion such as via an eccentric cam to drive the blade set (50). The details of the drive system (30) are generally known in the art and alternative known designs may be implemented provided they provide the needed power, reciprocation rate and can be easily incorporated into a hand held housing (20). As noted above a Pacific International Tool & Shear, Kingston, Wash. (Model No. SS504) forms an acceptable base for tool (10), this is also known as PacTool International and sell under the SNAPPER SHEAR™ brand for shear based tools.

The blade set (50) may consist of a left static cutting blade (51) mounted on the left side of the head (40), a right static cutting blade (52) mounted on the right side of the head (40) and a dynamic blade (53) pivotally coupled between the left (51) and right (52) static cutting blades. The blade set (50) can be formed of any suitably hard material; however tool steel is likely due to the ability to maintain a sharp shearing or cutting edge. Tool steel refers to a variety of carbon and alloy steels that are particularly well-suited to be made into tools. Their suitability comes from their distinctive hardness, resistance to abrasion, their ability to hold a cutting edge, and/or their resistance to deformation at elevated temperatures (red-hardness). With carbon content between 0.7% and 1.5%, tool steels are manufactured under carefully controlled conditions to produce the required quality well suited for holding the tight tolerances needed for blade set (50). A typical blade set (50) will maintain a high level of sharpness sufficient for about 50 automotive windshields, after which the blades can be refurbished for further use.

The reciprocating motion provided by the transmission (32) inside the head (40) drives the dynamic blade to generate cutting forces on the work piece W against the left (51) and right (52) static cutting blades. The head (40) encompasses the blade set (50) using the forward fastener set (42), the middle fastener set (43) and the aft fastener set (44).

Figure 2:
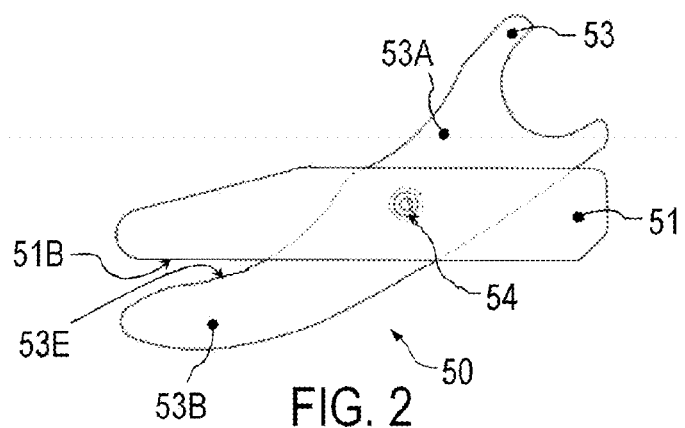
FIG. 2 is a schematic side elevation view of the blade set of FIG. 1.
Figure 3:
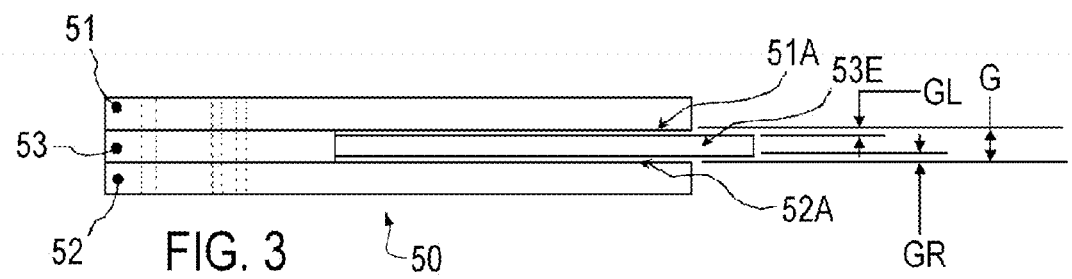
FIG. 3 is a schematic top plan view of the blade set of FIG. 1.

FIG. 2 is schematic side view of the blade set (50) and FIG. 3 is a schematic plan view of the blade set (50) used with the laminated glass and film-covered glass cutting tool (10). The left static cutting blade (51) contains a right interior surface (51a) and a lower cutting surface (51b). The right static blade (52) contains a left interior surface (52a) and a lower cutting surface (52b). The dynamic cutting blade (53) contains a body (53a), a blade (53b), a left exterior surface (53c), a right exterior surface (53d) and an upper cutting surface (53e).

The cutting surfaces (left—51a, right—52a) of the static cutting blades (left—51 and right—52) and the cutting surface (53e) of the dynamic cutting blade (53) may contain straight, curved or variable shapes along their respective lengths and may contain concave, trapezoidal or variable shapes along their blade cross sections. The details of the dynamic cutting blade (53) are described in greater detail in connection with FIGS. 4-6.

FIG. 4 is a schematic side elevation view of a dynamic blade (53) of a modified blade set (50) for use in the laminated glass cutting tool (10) of FIG. 1 and FIGS. 5 and 6 are schematic side elevation views of the blade set (50) of FIG. 4 in a closed and open position, respectively to illustrate the stroke or bite of the tool (10). In FIG. 4 the dynamic blade (53) includes an opening (56) for bushing (54) to receive a pivot axel or there through. As best illustrated in comparing the cutting surface (53e) of the dynamic cutting blade (53) between the open and closed positions of FIGS. 6 and 5, the cutting surface (53e) includes a central main cutting section (57) that performs the substantial shearing, an immediate chip guiding surface (58) following the cutting section (57) and a guide in surface (58) immediately before the cutting section (57). The operating throat of the tool, as shown, moves between 0.566" and 0.285" in this embodiment and the tool is intended to take small, extremely rapid "bites" or cuts from the work piece. As shown, generally less than 20% of the effective blade length (distance from tip to the intersection of the cutting edges of the static blades (51 and 52) and the dynamic blade (53) in the open position of FIG. 6), forms the cutting section (57) and often 10-15% of the effective blade length forms the cutting section (57).

In front of the cutting surface (53e) is a lead in surface (60) that extends to a blunted tip (61), as shown. The blades (51, 52 and 53) of the blade set (50) include the blunted tip (61) construction as shown to facilitate using the tool (10) as a punch to gain initial access for the tool (10) in windshields, windows or other work pieces in which the work piece edge is not free. The operator will punch the tips (61) of the blade set (50) generally perpendicularly through such a glass work piece to form an initial opening and the lead in surface (60) allows the dynamic blade (53) to easily be slipped through such an initial opening to begin shearing operation.

The rear of the dynamic blade (53) includes a coupling (62) to engage with the reciprocating member, which may be a rotating eccentric cam. The shape of the coupling (62) is specific to the element forming the reciprocation to which it connects, and the illustrated version is one known example.

As shown in the FIGS. 4-6, in side view the static blades (51) and (52) have a straight cutting or shearing edge extending back from the blunted tip (61) extending at a sharp angle from the other side of the blunted tip (61) to the area of full thickness of the static blade (51 and 52) in the area across from where the shearing occurs such that the shearing is generally occurring at the thicker part of the blades (51 and 52). From this part of the blade (52 and 51) rearward the opposed sides are generally parallel as shown. The top or operating edge of the dynamic blade (53) was discussed above. The rear side of the blades (53) extends at a sharp angle from the other side of the blunted tip (61) from leading surface (60) to the area of full thickness of the blade (53) in the area across from the portion (57) where the shearing occurs such that the shearing is generally occurring at the thicker part of the blade (53). From this part of the blade (53) rearward the opposed sides are generally parallel as shown.

In the particular embodiments shown, the left static cutting blade (51) and right static cutting blade (52) of blade set (50) are mounted in a parallel fashion, on the same plane inside the head (40) using the forward (41), middle (42) and aft (43) fastener sets. The static blades (51 and 52) contain a gap (G) equivalent to 0.250 inches.

The forward fastener set (41) provides the pivot for dynamic cutting blade (53) which contains a bushing (54) in pivot opening (56). The dynamic cutting blade (53) pivots between the left (51) and right (52) static cutting blades and reciprocates between opened to closed positions shown in FIGS. 6 and 5, respectively, as powered by the drive system (30). The left exterior surface (53c) of the dynamic cutting blade (53) rests against the right interior surface (51a) of the left static cutting blade (51). The right exterior surface (53d) rests against he left interior surface (52a) of the right static cutting blade (52). The gap (GL) between the left static cutting blade (51) and the dynamic cutting blade (53) and the gap (GR) between the right static cutting blade (52) and the dynamic cutting blade (53) may be between 0.005-0.025 inches, respectively.

As discussed above, to allow access to a closed edge work piece W such as an automobile windshield, the operator gains access to the undersurface of the glass by jabbing the blade tips (60) into the windshield. When the laminated glass or film-covered glass work piece W is placed between the static (left—51 and right—52) and dynamic cutting blade (53) of the blade set (50), the work piece W is cut by the shearing forces developed as the upper cutting surface (53e) of the dynamic cutting blade (53) is powered to close against the lower cutting surfaces of the static cutting blades (left—51b and right—52b) of the left (51) and right (52) static cutting blades.

The chaff generated but the cutting action of the blade set (50) is ejected upward from the blade set (50) by the reciprocating action of the dynamic cutting blade (53). With the present blade set (50) design of tool (10) the chaff is largely sheared off as a continuous ribbon of material rather than being shredded into dangerous airborne particulates. The dust or particulate produced by tool (10) on a automotive window removal is reduced over 90% from conventional window cutting (ripping) saws. The chip guiding surface (59) of the cutting surface (53e) can be used to control and guide the chaff. The blade set (50) as shown will minimize air born silica dust which represents an additional hazard, particularly in windshield replacement applications.

In operation after the initial opening is formed (if needed), the operator grasps the handle (23) of the housing (20) and activates the motor control switch (22) causing the motor (30) to activate driving the transmission (32) causing the dynamic cutting blade (53) to reciprocate between opened and closed positions at a rate of about 0-2,500 RPM or higher.

First responders like fire fighters, police and emergency medical personnel often are required to remove the windshield or rear glass to gain access to vehicle occupants in need of emergency removal and/or medical care. Windshield repair/replacement technicians are required to cut the windshield glass to remove intact inspection stickers. Others involved with laminated glass and film-covered glass are required to cut the glass for a variety of purposes. In each case, the current methods have increased risk of injury and require significant amounts of time to complete. The current embodiment of this laminated glass and film-covered glass cutting tool will reduce the risk of injury to a trapped victim or the operator and greatly decrease the time necessary to perform the activity. Obviously decrease time is important in all environments, but in emergency response, decreasing the time that personnel take to reach a crash victim will substantially increase the survival rate and generally decrease the overall severity of wounds, as it is well It is well established that the patients chances of survival are greatest if they receive care within a short period of time after a severe injury, with the period after an injury sometimes referred to as the "golden hour." Windshield, passenger and rear windows of most automobiles can be removed in about 45 seconds with tool (10), and almost always less than 1 minute, for quick access to patients or for further rescue operations.

In addition to the speed of windshield removal with the tool (10) and the decrease in silica dust for the operator and patient, the tool (10) allows for one handed operation. This allows the other hand to be used, such as with a glass holding lifter, also known as handheld vacuum cups. Designed specifically for glass handling, vacuum cups are the standard of the glass industry and used by glaziers around the world. These vacuum cups put a handle where needed on flat glass, curved or bent glass, auto glass and even some pattern glass. Some cups use a pump to create a higher vacuum and thus a more reliable hold. Known vacuum cup models, such as available from WPG under the brand name WOOD'S POWR-GRIP® includes diameters from 1¼ to 10 inches and handles for every kind of glass handling, including fenestration, windshield replacement, processing and more. The tool (10) together with a vacuum cup allows a single operator (e.g. first responder) to safely and rapidly remove automobile windows as schematically illustrated in FIG. 7.

The tool is described as particularly useful for window removal for first responders or field replacement technicians; however it can be used for other similar articles. As an additional note for field replacement technicians to tool allows the technician to easily trim around inspection/emission stickers (or passes or other fixed emblems) on the replaced windshield, which sticker containing trimming can have edges taped with duct tape or the like and the inspection/emission sticker containing unit left with the vehicle, avoiding the need for the user to obtain replacements for these immediately.

From the foregoing it will be appreciated that, although specific embodiments of the invention have been described herein for purposes of illustration, various modifications may be made without deviating from the spirit and scope of the invention. For example, the left and right static cutting blades may be attached to the motor unit instead of the head. Accordingly, the invention is not limited except as by the claims.

What is claimed is:

1. A method of cutting laminated glass and film-covered glass including the steps of:

Coupling a handhold to a laminated glass or film-covered glass work piece;

Placing the laminated glass or film-covered glass work piece in between static cutting blades and a reciprocating cutting blade of a blade set of a handheld cutting tool while a lower surfaces of the static cutting blades are against an upper surface of the work piece; and Simultaneously holding the handhold to hold the work piece and activating a handheld cutting tool trigger switch which activates the reciprocating cutting blade from the open to closed position consecutively against the under surface of the work piece causing work piece cutting progressively; and wherein generally less than 20% of a distance from a tip of each blade to the intersection of the cutting edges of the static blades and the dynamic blade in the open position forms a cutting section for the tool.

2. The method of cutting laminated glass and film-covered glass of claim 1, wherein the operator uses a handheld vacuum cups to form the handhold to hold the work piece while cutting the work piece.

3. The method of cutting laminated glass and film-covered glass of claim 1, wherein a chaff removed is sheared off as a substantially continuous ribbon of material.

4. The method of cutting laminated glass and film-covered glass of claim 1, wherein a gap between the static cutting blades and the dynamic cutting blade is between about 0.005-0.025 inches.

5. The method of cutting laminated glass and film-covered glass of claim 4, wherein the reciprocating cutting blade has an effective width between 0.165 and 0.249 inches.

6. The method of cutting laminated glass and film-covered glass of claim 1, wherein the work piece removed in about 45 seconds.

7. The method of cutting laminated glass and film-covered glass of claim 6, wherein generally less than 20% of a distance from a tip of each blade to the intersection of the cutting edges of the static blades and the dynamic blade in the open position forms a cutting section for the tool.

8. The method of cutting laminated glass and film-covered glass of claim 6, wherein a gap between the static cutting blades and the dynamic cutting blade is between about 0.005-0.025 inches.

9. The method of cutting laminated glass and film-covered glass of claim 8, wherein the reciprocating cutting blade has an effective width between 0.165 and 0.249 inches.

10. The method of cutting laminated glass and film-covered glass of claim 1, wherein each blade includes a blunted tip.

\* \* \* \* \*